United States Patent
Anderson et al.

(10) Patent No.: US 8,675,900 B2
(45) Date of Patent: Mar. 18, 2014

(54) HEARING SYSTEM AND METHOD AS WELL AS EAR-LEVEL DEVICE AND CONTROL DEVICE APPLIED THEREIN

(75) Inventors: Blane Anderson, Burnsville, MN (US);
Larry Hagen, Wayzata, MN (US);
Randall Roberts, Eden Prairie, MN (US)

(73) Assignee: ExSilent Research B.V., Amsterdam (NL)

( * ) Notice: Subject to any disclaimer, the term of this patent is extended or adjusted under 35 U.S.C. 154(b) by 671 days.

(21) Appl. No.: 12/794,141

(22) Filed: Jun. 4, 2010

(65) Prior Publication Data
US 2011/0299709 A1    Dec. 8, 2011

(51) Int. Cl.
*H04R 25/04*    (2006.01)
*H04R 25/00*    (2006.01)
*H04R 29/00*    (2006.01)

(52) U.S. Cl.
USPC .............................. 381/315; 381/314; 381/60

(58) Field of Classification Search
USPC .................... 381/315, 314, 320, 321, 60, 316
See application file for complete search history.

(56) References Cited

U.S. PATENT DOCUMENTS

| | | | |
|---|---|---|---|
| 5,197,332 A | | 3/1993 | Shennib |
| 5,710,819 A * | | 1/1998 | Tøpholm et al. ............. 381/316 |
| 6,115,478 A * | | 9/2000 | Schneider ..................... 381/314 |
| 6,118,877 A * | | 9/2000 | Lindemann et al. ........... 381/60 |
| 6,366,863 B1 * | | 4/2002 | Bye et al. ....................... 702/57 |
| 6,674,862 B1 * | | 1/2004 | Magilen .......................... 381/60 |
| 6,694,034 B2 * | | 2/2004 | Julstrom et al. .............. 381/315 |
| 6,788,790 B1 * | | 9/2004 | Leysieffer ....................... 381/60 |
| 6,895,345 B2 * | 5/2005 | Bye et al. ........................ 702/57 |
| 7,016,504 B1 * | 3/2006 | Shennib .......................... 381/60 |
| 7,058,182 B2 * | 6/2006 | Kates ............................... 381/60 |
| 7,068,802 B2 * | 6/2006 | Schulz et al. ................. 381/318 |
| 7,223,245 B2 * | 5/2007 | Zoth et al. ..................... 600/559 |
| 7,349,549 B2 * | 3/2008 | Bachler et al. ............... 381/314 |
| 7,366,307 B2 * | 4/2008 | Yanz et al. ...................... 381/60 |
| 7,688,983 B2 * | 3/2010 | Voix et al. ....................... 381/60 |
| 8,194,864 B2 * | 6/2012 | Goldstein et al. .............. 381/56 |
| 8,196,470 B2 * | 6/2012 | Gross et al. ..................... 73/585 |
| 2005/0018858 A1 * | 1/2005 | John ................................ 381/60 |
| 2005/0094822 A1 | 5/2005 | Swartz |
| 2007/0195965 A1 * | 8/2007 | Thomasson et al. ........... 381/60 |
| 2008/0240452 A1 * | 10/2008 | Burrows et al. ................ 381/60 |
| 2008/0260171 A1 * | 10/2008 | Nordahn et al. ............... 381/60 |
| 2010/0137739 A1 * | 6/2010 | Lee et al. ...................... 600/559 |
| 2010/0158262 A1 * | 6/2010 | Schumaier et al. ............ 381/60 |

(Continued)

FOREIGN PATENT DOCUMENTS

WO    2007009287    1/2007

*Primary Examiner* — Edgardo San Martin
(74) *Attorney, Agent, or Firm* — Young & Thompson

(57) ABSTRACT

An ear-level hearing device and a handheld computer with a graphical user interface determines a subject's own hearing threshold. Hardware includes the smartphone, viewing screen of the smartphone, smartphone software, ear level hearing device, transmitter on the smartphone and receiver on the ear level device (ELD) communicating with the graphical user interface on the smartphone to the ear level hearing device. The interface on the smartphone may include an automatic routine or buttons to vary frequency and amplitude of a frequency dependent sound presentation to the earpiece. Software installed on the hand-held smartphone system sends wireless signals to the ELD changing acoustic parameters in the listening device. The ELD stores frequency/amplitude parameters of the thresholds and wirelessly delivers them to the smartphone. The smartphone uses the threshold data to derive the appropriate amplified acoustical signal (relative to the thresholds) to the subject.

19 Claims, 8 Drawing Sheets

(56) References Cited

U.S. PATENT DOCUMENTS

| | | | |
|---|---|---|---|
| 2010/0202625 A1* | 8/2010 | Boretzki et al. | 381/60 |
| 2010/0246866 A1* | 9/2010 | Swain et al. | 381/315 |
| 2011/0176697 A1* | 7/2011 | Apfel et al. | 381/314 |
| 2011/0222696 A1* | 9/2011 | Balachandran et al. | 381/58 |

* cited by examiner

HEARING SYSTEM AND METHOD AS WELL AS EAR-LEVEL DEVICE AND CONTROL DEVICE APPLIED THEREIN

FIELD OF THE INVENTION

The present invention relates to a hearing system comprising an ear-level hearing device having an electro-acoustic transducer communicating with an ear canal of a subject, which transducer is driven by programmable sound processing means on basis of a programmable sound processing scheme, and comprising a control device to customize said sound processing scheme at least in part to said subject. More particularly, this invention relates to the programming of assistive listening devices.

BACKGROUND OF THE INVENTION

Traditionally, assistive listening devices have existed to improve the hearing of the hearing impaired population. Today, these devices are very sophisticated. Computer technology abounds in the field of assistive listening devices. Tiny computer chips that are programmable by audiologists and other hearing professionals exist in these ear-level devices. Professionals are employed to program the devices for their patients and patient input to the device's "best fit" are mostly subjective.

It is very rare indeed that a hearing impaired person has identical amounts of loudness loss at all pitches. Most commonly, patients exhibit dissimilar amounts of hearing loss (inability to hear at certain pitches) at various frequencies. For example, an individual's hearing loss may be greater at the high frequencies when compared to the low frequencies. Hearing health professionals make measurements to determine the extent of an individual's hearing impairment. With these measurements, programmable parameters for fitting a hearing device are determined. These parameters are typically adjusted by means of a computer graphical interface that the hearing professional uses to customize the hearing instrument to the patient's hearing needs. In addition, countless formulae to customize the acoustical needs of the patient have been derived by universities, hearing scientists and hearing instrument manufacturers.

Measurement and interpretation of auditory threshold is traditionally done through audiometry that is administered by a specialist of the hearing field or an audiologist. In most cases, it is the audiologist's responsibility to record the threshold data and then to recommend amplification that is correct for the hearing impaired individual. Many times, however, the audiologist's job is confounded by inconsistencies such as patient perception, patient cooperation during testing, audiologic equipment, hearing instrument manufacturer software hang-ups and unrealistic patient expectations. In short, it can be a daunting task to test the hearing, recommend the amplification and then fit the hearing device to the patient's ear.

For the ambitious practitioner, testing does not stop once the audiometry is done. These individuals may use direct measurement of the hearing instrument while it is in the patient's ear canal. Such testing is called real ear testing. For this objective measure, a probe microphone is placed into the ear for direct observation of the sound pressure level in the ear canal. This is done while the hearing instrument is in the auditory meatus (or otherwise called in-situ). However, this direct measurement is often inconsistently assessed because of difficulties with hearing instrument placement, probe microphone position in the canal, reference microphone placement, calibration of the sound field and even sound field noise. In short, it is difficult to absolutely know the sound pressure of the ear canal as a hearing instrument is being used. Without confidence in the measurements one certainly is without confidence in his/her ability to assess the utility of the amplification.

For these and other reasons, the present invention aims inter alia to provide a hearing system and method for a relatively easy self-administered audition threshold determination.

SUMMARY OF THE INVENTION

To that end a hearing system of the type described in the opening paragraph according to the invention is characterized in that recording means are provided to record a drive signal between said sound processing unit and said transducer, in that said control means comprise a temporary control device held by a user enabling the user to select auditory signals at different amplitudes, in that said control device and said ear-level hearing device are provided with communication means to communicate user selected auditory signals to said transducer and to exchange corresponding drive signals as recorded by said recording means with said control device, in that said control device comprises an algorithm to translate threshold responses of said user in response to said auditory signals into a customized sound processing scheme, and in that said control device is provided with programming means to pass said customized sound processing scheme to said sound processing device.

Specifically, the system according to the invention incorporates a self-administered test whereby the subject listens to a number of frequency specific tones at varying frequencies (psycho acoustic parameter is pitch) and varying amplitudes (psycho acoustic parameter is loudness), like one-third octave narrow band noises or tone bursts, in order to find the softest sound that the subject can hear. These data are used in the programming of the assistive listening device (hearing aid) to customize the sound to the listener.

Though this invention is not meant to challenge the utility of traditional audiology and hearing aid fitting, it does offer a unique and direct way to obtain patient hearing threshold and then to prescribe correct amplification from an algorithm specific to the invention.

The system according to the invention is based on a hearing device that directly allows a subject to measure the subject's own threshold of hearing through a software user interface installed on the control device, particularly a smart phone, PDA or any other digital processing device (computer). In an embodiment, the control device and ear level hearing device work in tandem. The ear level device produces discrete noises at different frequencies, like (one-third octave) narrow band noises or tone bursts, that lay within the hearing frequency range of the human ear. These noises are presented in ascending and descending amplitudes. The subject adjusts up and down these amplitudes until the subject finds the sound level that is just barely audible. Alternatively the device software may present these sounds automatically with an ascending amplitude. Voltages across the transducer in the ear level device that produces the sound in the ear are then measured and are recorded in a software database. These are the direct thresholds of the subject as measured in voltage; the thresholds are the voltages needed to elicit a threshold sound pressure level inside the ear canal of the individual. It must be understood that these are relative measurements in terms of voltage, of that given ear, using this particular ear level device that includes a particular transducer.

In addition, the system contains another algorithm that uses as input the patient's user threshold data to prescribe real ear sound pressure level most appropriate for the subject at supra threshold levels (the prescription needed for the individual's hearing loss).

For clarification, it must be noted that these threshold data cannot be transferred or referenced in any way with another subject's data—they are specific and are only relevant to the test subject.

These and other embodiments, aspects, advantages, and features of the invention will be set forth in part by the description that follows.

DETAILED DESCRIPTION OF THE INVENTION

The following detailed description, reference is made to many drawings that endeavour to illustrate, in specific, the function of the invention. Through these drawings, most of the essence of the device is exemplified. In the drawings.

Figure 4:
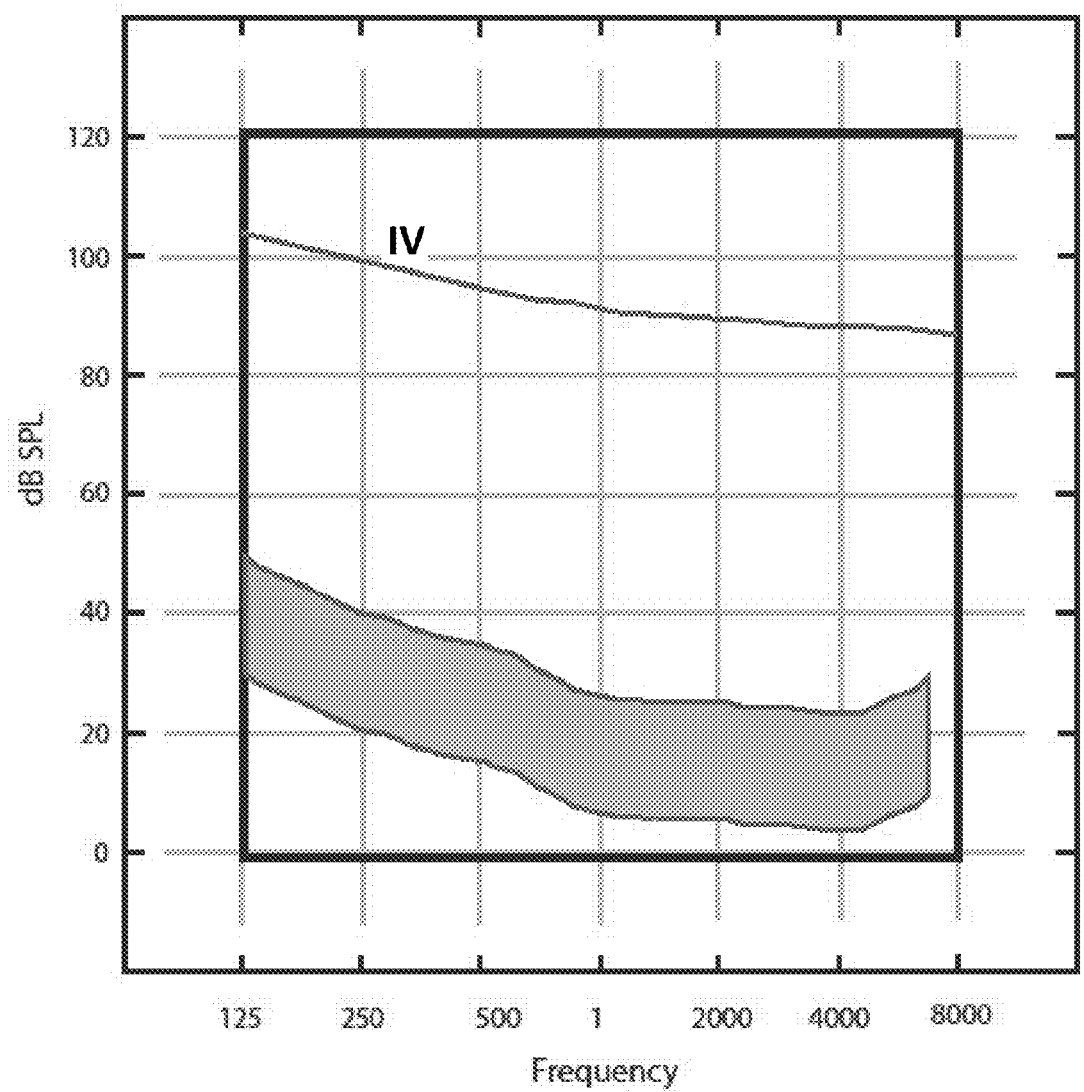
Figure 5:
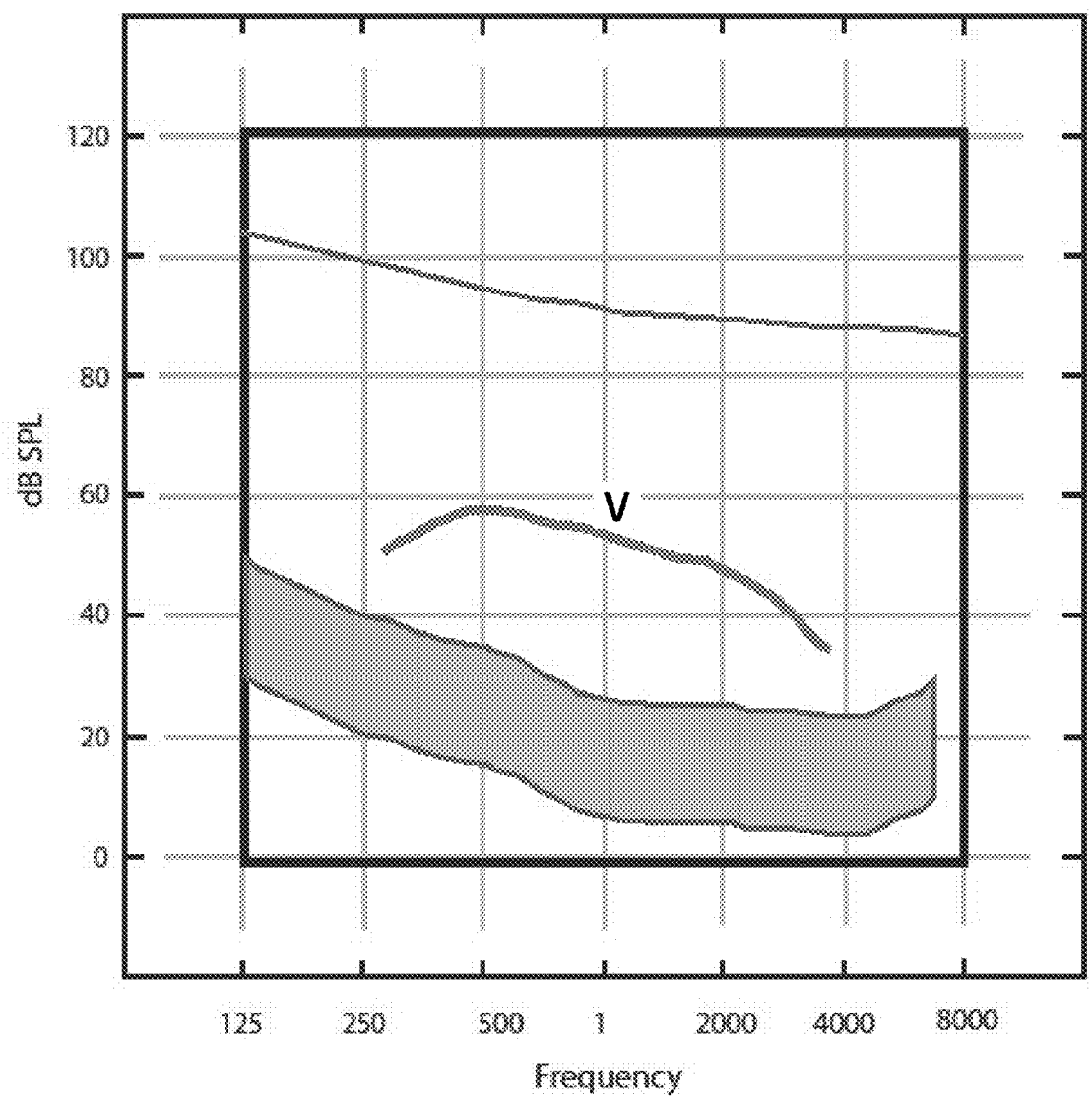
Figure 6:
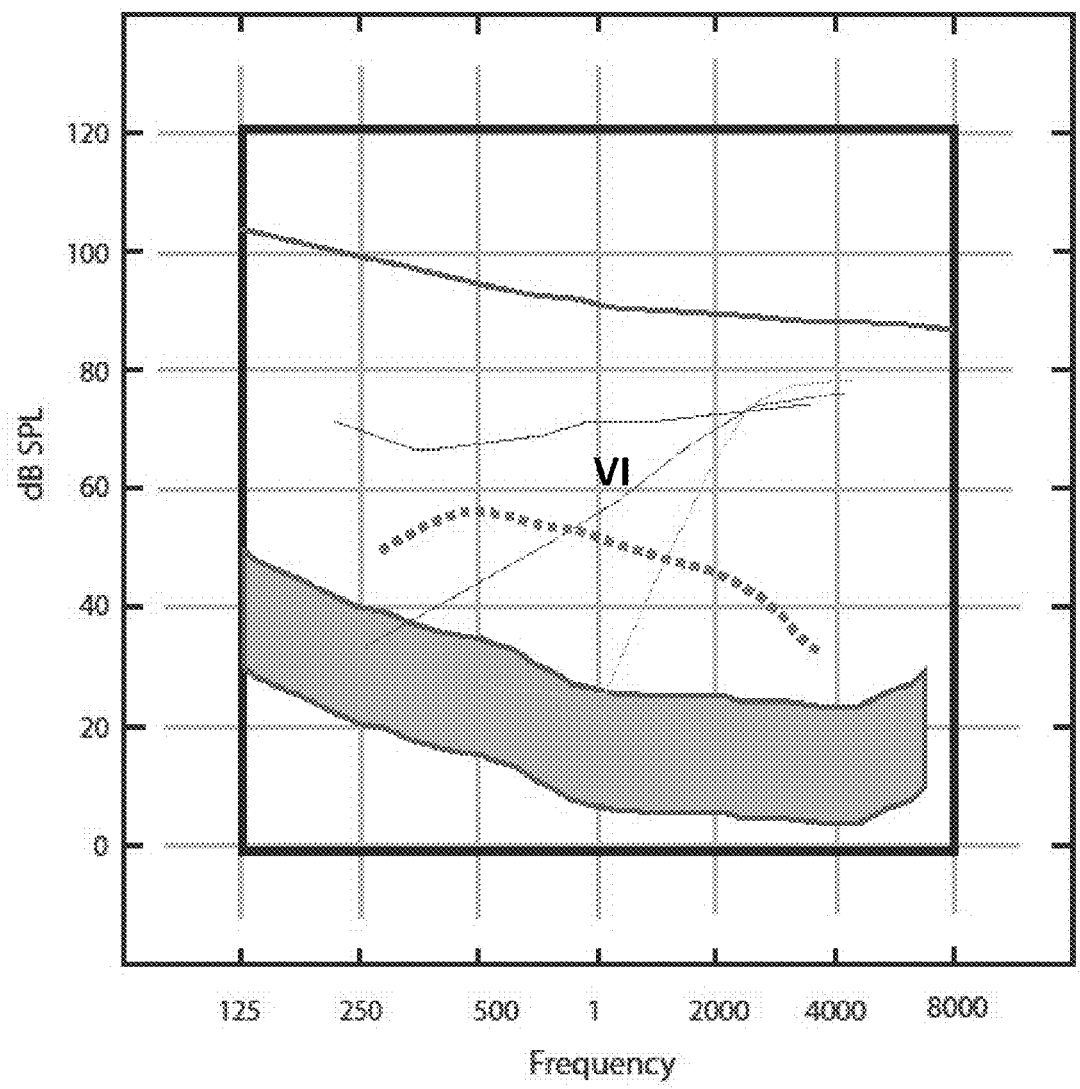
Figure 7:
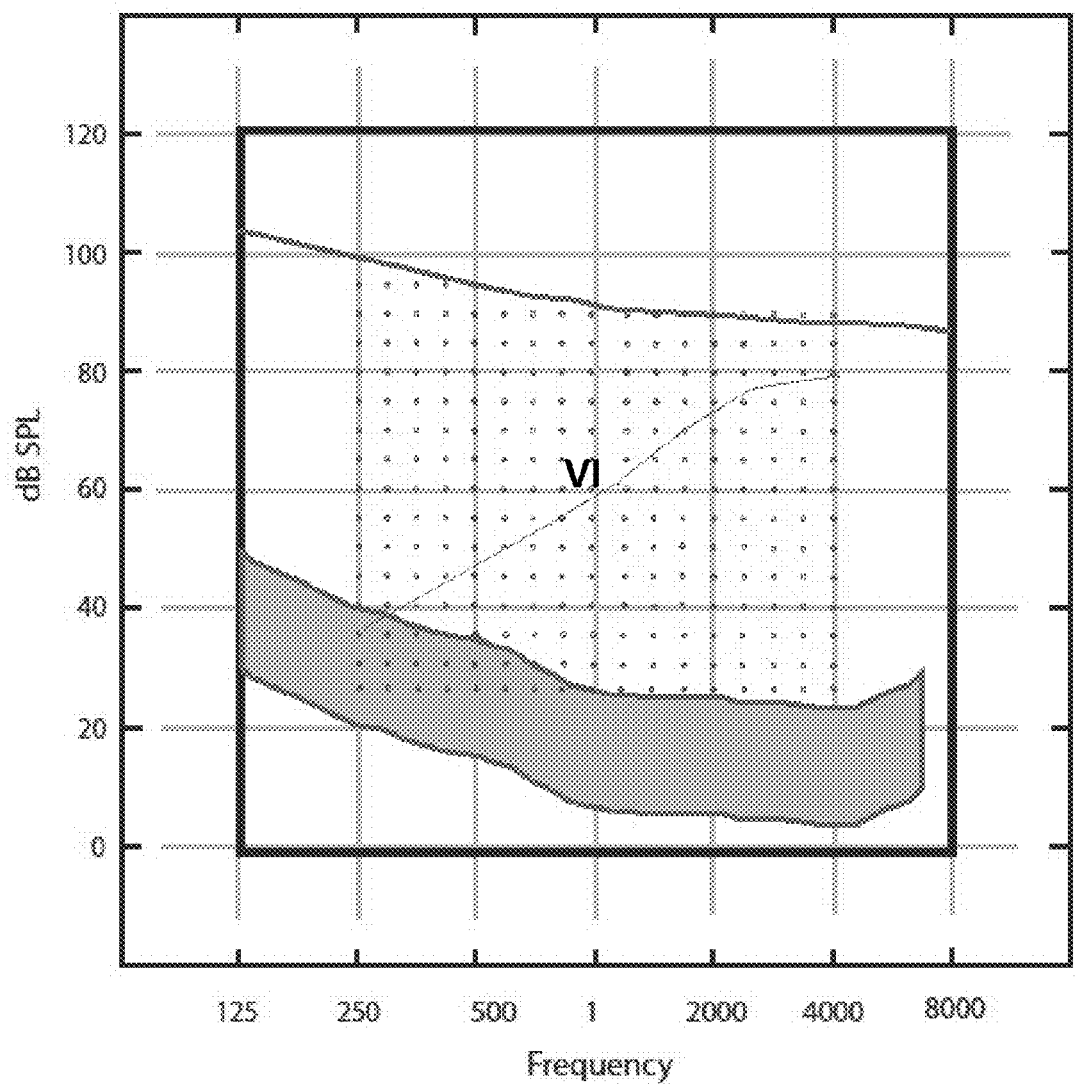
Figure 8:
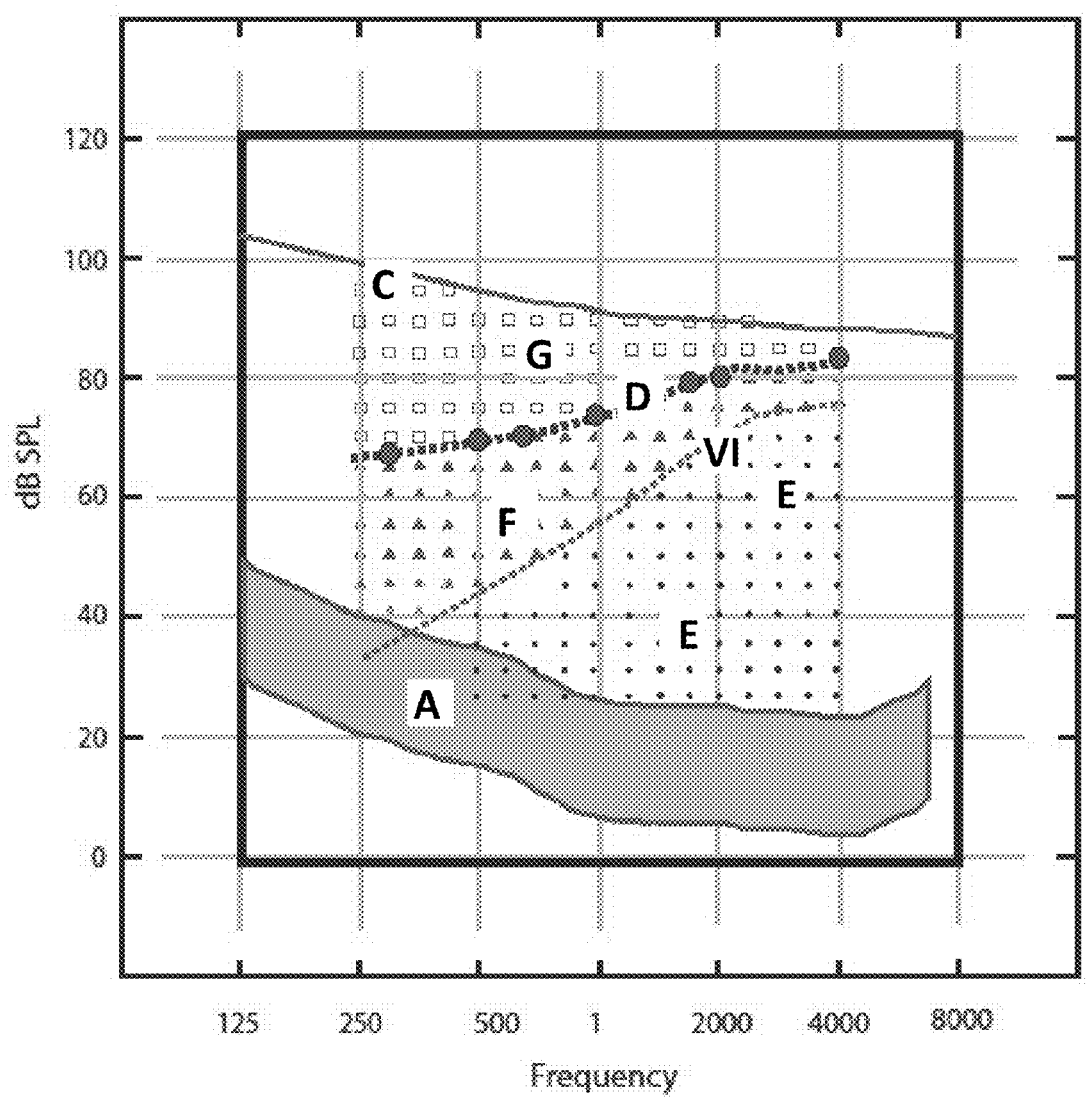

FIG. 4 displays the UCL or the uncomfortable level of hearing;

FIG. 5 plots the Long Term Average Speech Spectrum for average speech;

FIG. 6 presents three types of hearing losses (in dB SPL) that have common nomenclature between hearing healthcare professionals;

FIG. 7 depicts a sloping hearing loss that is laid on top of a number of amplitude coordinates in the frequency domain (small round circles); and FIG. 8 illustrates how inaudible and barely audible sounds must be amplified according to the system's prescription fitting algorithm In essence, the ear-level device is a portable personal listening mechanism. Although the invention is equally well applicable, the invention will be described in this example along an ear-level device, see FIG. 1, that consists of a first part 1, which fits and resides behind an ear 10 of an individual, and a second part 2, which fits and resides in the ear canal of the individual, which parts 1,2 communicate with each other over a connecting cable 3. Said cable moreover provides any necessary electric power to the in-ear part or piece 2 of the device, fed from a (rechargeable) battery fitted in the behind-the-ear part 1.

The device of this embodiment includes a microphone to detect environmental sounds and sound processing means, including an analog to digital converter (ADC) converting an output signal of said microphone, an amplifier for digital amplification with algorithms to process incoming sounds, and a digital to analog converter (DAC) to generate an output drive signal. Said drive signal is fed to a small speaker (known as an electro-acoustic transducer or receiver in the field of hearing device manufacturing) of said ear-level device to deliver the amplified sound to the ear canal of the subject/user. The microphone and speaker are both accommodated in the in-ear part 2 of the device, whereas the sound processing means reside in the behind-the-ear part 1 of the system. I should be noted however that an alternative distribution of the functional components of the system over both parts 1,2 of the ear level device is likewise feasible within the context of the invention.

This ear level device also employs a Bluetooth receiver capable of receiving software commands from a control device which in this embodiment consists of a smart phone, PDA or other hand held computer device, all of which hereinafter are briefly referred to as smart phone, loaded with auditory software according to the invention. Alternatively an other wireless data transmission protocol may be implemented, either in standard form or of proprietary nature. The smart phone's graphical user interface (GUI) 20 shall be described later along FIG. 2 of the drawings. The ear level device is capable of producing frequency specific sounds, like in this case narrow band noises, needed to assess the subject's threshold of hearing. Instead of narrow band noises for instance also frequency specific tone bursts may be employed for this purpose. The ear level device then transmits the threshold data back to the smart phone for analysis. The user interacts with the software to produce narrow band noise sounds in the ear. Acoustical parameters are communicated from the smart phone device to the ear level device via the wireless Bluetooth protocol.

Figure 1:
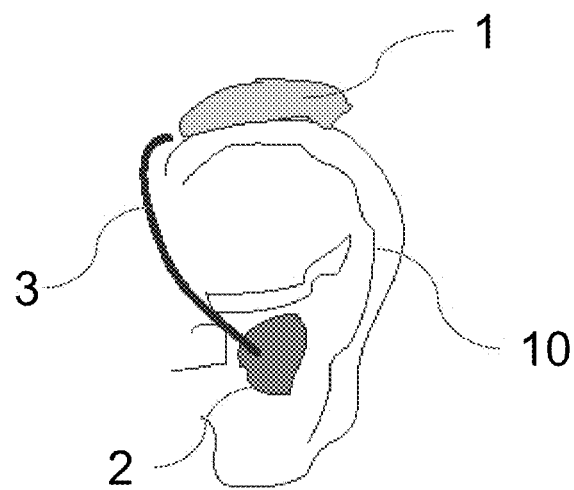
FIG. 1 shows an ear-level device of the invention.

An important aspect of this ear-level device is its ear tip 2, see FIG. 1, that fits securely inside the ear canal. The ear tip is designed to accept a number of soft, mushroom type plugs, sized at various diameters, that help to block out environmental sounds and also prevent sound from leaking out of the ear canal. The ear tip with plug combination preferably is able to attenuate 15 dB in the low frequency range, i.e. less than 1000 Hz, in order to be effective when the individual listens to test sounds. In order words the device preferably attenuates at least 15 dB re: the open ear canal.

Amplitude and frequency parameters are controlled by the subject and are directed to the ear-level device wirelessly. The subject controls the ear level noises by using arrow buttons 21 . . . 24 to control increasing and decreasing frequency and amplitude values, see FIG. 2. Alternatively the device 20 might submit these signals automatically with an increasing amplitude to the user's ear. These changes of frequency and amplitude parameters are communicated from the smart phone device to the ear level device via the wireless Bluetooth protocol. It should be noted that instead of Bluetooth also any other, particularly a proprietary, wireless means may be used for the data exchange between the ear level device and the PDA device.

The user of the control device can change the amplitude (psycho acoustic parameter is loudness) of the noises by means of the software interface. By adjusting the amplitude in terms of louder and softer, the subject ascertains the softest level that the subject can hear. In addition, the user of the device can change the frequency (psycho acoustic parameter is pitch) in order to obtain the threshold frequency spectrum in terms of narrow band noise of the subject's hearing thresholds. These values are then transmitted to the smart phone and saved in a software database.

Figure 3:
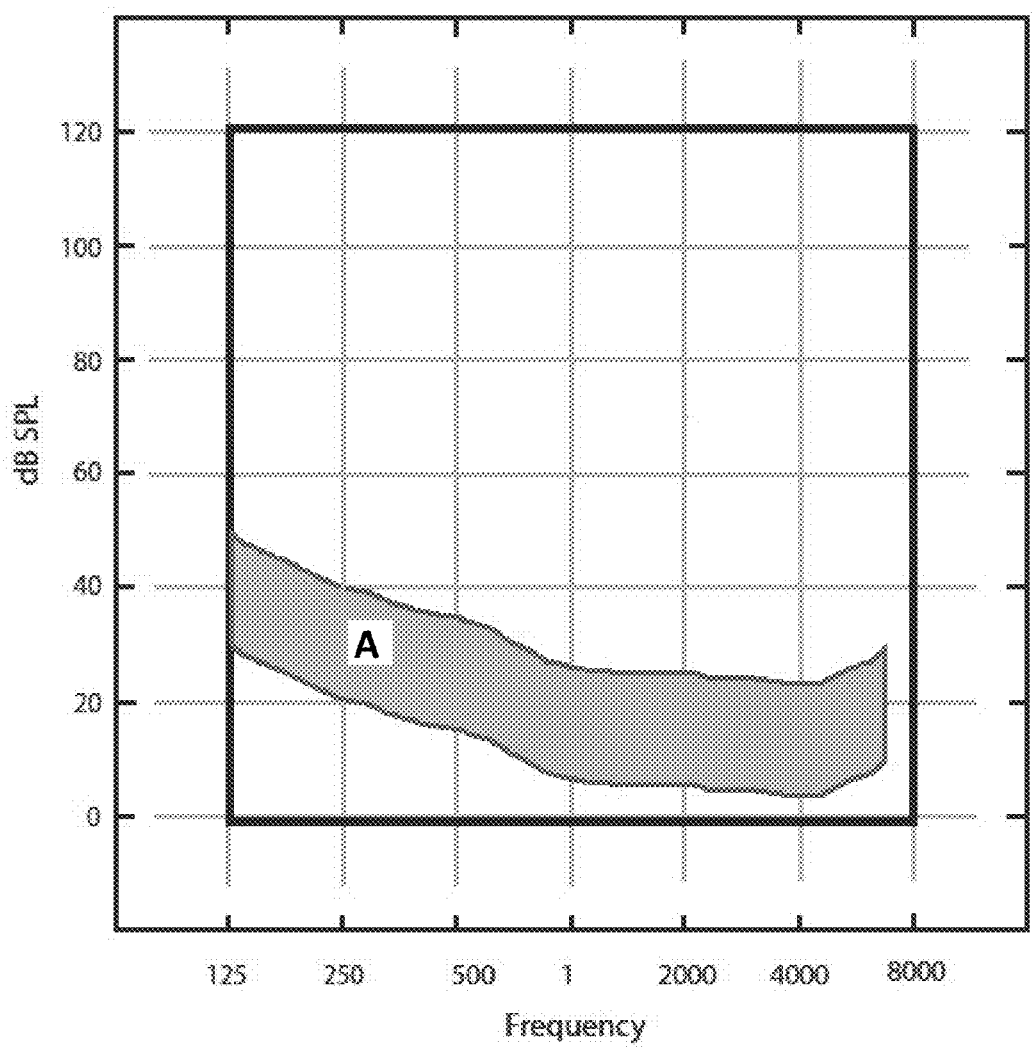
FIG. 3 is a graph of the normal range of hearing (NRH)

Throughout the years many investigators have determined the normal range of hearing. This range is depicted in FIG. 3 with a 20 dB range as measured in dB Sound Pressure Level (re: 20 mPa). Today it is defined by an ANSI 1963 standard and the range shown in FIG. 3 is representative of this standard.

The term "normal hearing" in humans refers to that part of the population that exhibits no hearing problems, that is, it is a population with no history of ear disease, ear trauma, hearing loss due to old age (presbyacusis) or hearing loss due to noise exposure. Normal hearing is measured in terms of dB Hearing Level (dB HL) or dB Sound Pressure Level (dB SPL).

One is said to be "normal" if the subject's hearing is 20 dB HL or below (e.g., 5 dB HL, 10 dB HL). This indicates that the subject can hear very soft sounds clearly. One is said to have a "hearing loss" if their auditory thresholds, as described above, are greater than 20 dB HL. The greater the difference is from 20 dB HL, the more severe the hearing loss.

FIG. 4 displays the uncomfortable level of hearing (UCL), reflected by line IV. It is measured by the subject's subjective response to loud sound presentations to the ear. Again, throughout the years investigators have found mean UCLs dependent on the degree of hearing loss.

UCL measurements are important in the field of hearing aid fitting because the audiologist or hearing professional does not want to exceed the UCL of a patient when picking a hearing device. It is also an important aspect in the invention because it sets a limit of the electrical response that shall be described below.

FIG. 5 plots the Long Term Average Speech Spectrum (LTASS) for average speech, reflected by line V. This spectrum is a composite of all talkers—children, women and men speaking at an average SPL. It is the job of the hearing healthcare clinician to make the LTASS discriminate to the hearing impaired patient. By doing so through amplification, the patient is able to access speech sounds that are below the subject's threshold in an effort to making speech clearer. It is also necessary to amplify those parts of the speech spectrum that may lie above the threshold of the listener but may not be clear to the listener, e.g., very soft sounds.

FIG. 6 presents three types of hearing losses (in dB SPL) that have common nomenclature between hearing healthcare professionals. Hearing impairment refers to conditions in which individuals are fully or partially unable to detect or perceive at least some frequencies at a 20 dB normal hearing level (HL). This impairment is significant because it affects speech perception in these individuals. One is said to have a "hearing loss" if their auditory thresholds, as described above, are greater than 20 dB HL. The greater the difference is from 20 dB HL, the more severe the hearing loss. FIG. 6 describes three common types of hearing loss—precipitous, sloping and flat.

According to the invention, the subject's hearing threshold is measured subjectively in the subject's ear, using the ear-level device. It must be understood that the system according to the invention is not intended to measure the subject's hearing loss (or lack thereof) in comparison with "normal hearing" or any type of hearing loss. In a standard test, a subject's thresholds are measured with an audiometer where the earphone that presents the test tones are calibrated to that audiometer. Thresholds are then measured to ANSI standardized values so that the subject's hearing can be compared with that of "normal" hearing. Instead, with the device according to the invention, the threshold of the individual with the ear level device in the subject's ear is relevant only. The hearing data that are gathered are for that ear only, with the device worn comfortably at a given depth into the ear canal, using the test signals of the control device driven automatically or on demand to the one particular transducer of the ear level device. Thus, these test results and responses elicited by the wearer of the device are "subject ear specific".

Several types of hearing loss may be distinguished. A precipitous hearing loss is one that is contained mainly in the high frequencies. Though in the area below 1000 Hz the patient is hearing normally, the subject still will have problems with speech discrimination because many of the high frequency consonant sounds of speech (the consonant sounds above 1000 Hz contain most of the information that is necessary to discern speech) will be inaudible. Thus, it is important to amplify in the high frequency region.

A sloping hearing loss is one that demonstrates a mild hearing loss in the low frequencies and a moderate to severe loss in the high frequencies. This loss is completely out of the normal range of hearing. Here, it is important for the clinician to emphasize amplification in both the low and high frequency range.

A flat hearing loss is one that has a moderate to severe loss in both the low and high frequencies. Here, it is important for the clinician to provide amplification in both the low and high frequency ranges in order for the patient to hear syllabic and high frequency consonant information.

Traditional Real Ear Insertion Gain Versus Invention's Direct Real Ear Output

Traditional Real Ear Insertion Gain (REIG) is defined as the difference in gain between open ear canal gain and Real Ear Aided Response gain with the hearing device in-situ, i.e. in the ear. Traditionally, to amplify the patient appropriately, the clinician needs to do many measurements and calculations in order to prescribe the correct real ear gain for the patient.

The following examples reflect the usual (REIG) protocol and the Direct Real Ear Output (DREO) protocol, in accordance with the present embodiment of the invention, respectively:

Real Ear Insertion Gain (Traditional)
1. Take audiogram (thresholds of patient taken under earphones in dB Hearing Loss)
2. Pass audiogram through a formula that prescribes what (enhanced/amplified) sound is right for a specific impaired ear
3. Hearing aid presents the sound that is prescribed
4. Many factor conversions need to be considered before prescription is applied
   a. Conversion from dB SPL (sound pressure level) with insert earphone in ear to dB HL (hearing level).
   b. Subjective patient measurement of dB HL by means of insert earphones. This measurement assumes that the audiometer and earphones are properly calibrated so that the measurement in dB HL is precise.
   c. Calculation of prescription by means of a formula for Real Ear Insertion Gain dB per frequency/per input level.
   d. Measurement of the Real Ear Insertion Gain.

Many of these measurements and conversions introduce errors because of imprecision and estimation, i.e., incorrect prescription method, improperly calibrated audiometer, inaccuracy of clinician measurements, errors in conversions, etc.

Direct Real Ear Output (Specific to this Embodiment of the Invention)
1. Have the patient or the PDA control the SPL (sound pressure level) in his ear of a frequency specific signal, like narrow band noise (NBN), at various frequencies.
2. Provide a control device/apparatus, for instance a smart phone, PDA or hand held computer attached wirelessly to a separate ear level device, that enables the patient to vary the intensity, positively and negatively, of the NBN presentation at each frequency.
3. Thresholds are procured by positively and negatively varying the drive signal, particularly the voltage, of the electroacoustic transducer (speaker) that is closed off in the ear until the subject "brackets" the voltage that drives the transducer so that the patient can barely hear the signal.
4. Through software, have the patient listen for the very faintest sound that he can hear and tell the patient to acknowledge it by means of a virtual push button that is part of the sensitivity interface. This is to find the actual hearing threshold.
5. The software records the voltage over the transducer (drive signal) at which the response to the acoustic threshold stimulus is elicited. This describes how the acoustic threshold is elicited by means of the voltage variations on the transducer and what the system records (voltage) as the threshold.

As an example of for the present embodiment of the invention the sloping hearing loss, reflected in FIG. 6 by line VI, shall be used as demonstrative in that it is very representative of a hearing loss commonly seen in the audiology clinic. This sloping loss shall be measured in dB voltage relative to the voltage that drives the transducer.

FIG. 7 depicts a sloping hearing loss VI that is laid on top of a number of amplitude coordinates in the frequency domain (small round circles). The function of the hearing loss can be described in terms of these coordinates that it crosses. This is an important aspect of the invention in that it is these coordinates that are measured directly by the device.

This sloping hearing loss represents the thresholds, or just audible sounds, of the hearing impaired subject. These thresholds are not measured by traditional means using an audiometer. Instead, these are thresholds taken directly from the ear-level device and are measured in terms of the voltage that is needed to drive the transducer (speaker) that is in the ear-level device and is directing sound to the subject's ear canal.

As a transducer produces a sound pressure, a fixed voltage that is applied to it produces a fixed sound pressure level. As voltage goes up, so does sound pressure. This is a direct relationship, though, for most transducers, it is not a linear function. Also, this function varies dependant on the sound pressure frequency or other spectral shape. Most importantly, there is a one-to-one relationship between a transducer's voltage and SPL at a particular spectrum level.

Since there is a direct relationship between the amount of voltage and sound pressure for any given transducer and spectrum, a patient's threshold, or sound pressure needed to barely elicit a patient's response, can be measured directly by measuring the voltage needed to produce that response of a certain sound pressure level that is produced by that voltage. Another direct measure of the threshold can be interpreted as the amount of voltage applied to the transducer.

When a transducer is part of the plug apparatus, and a subject varies the voltage of the transducer in order to elicit a threshold response, the transducer can deliver x dB SPL at x frequency and with the patient responding, the actual sound pressure needed to elicit a threshold response can be recorded in terms of the voltage needed to elicit that sound pressure level. This direct measurement of patient threshold is not subject to the variances of audiometry (dB HL/clinician error/headphone/earphone correction factors/calibration of the equipment/5 dB step size, etc.), fitting formulae, calibration and the like.

The threshold is also dependent on the conductive characteristics of the middle ear transmission path. The system according to the invention does not take into account a measurement traditionally called in audiometry "air/bone gap." However, since loudness measurements are discrete and take into consideration the degree of bone conduction hearing loss, the device can help the individual who has an "air/bone gap."

Obtaining Subject's Thresholds

The subject shall place himself in the quietest room in his house. Ideally, the ambient noise should not be more than that in a quiet library in order to get accurate thresholds. Wearing the ear-level devices, the subject shall start the threshold software that will measure the subject's hearing thresholds.

The subject determines threshold without any need for a clinician. With the device in the ear, and the subject's use of a smart phone, or other communication device, the ear level device receives commands for frequency-specific audio data (e.g. narrow band noises) from the smart phone to be elicited by the ear level device at various presentation levels.

These measured levels are logged as threshold data in terms of transducer (earphone) output as measured in voltage. At different frequencies, it will take specific discrete voltages to drive the output device in the ear to the subject's actual threshold. These frequency specific voltages are then stored in a program application on the smart phone.

By means of subjective responses, the subject controls the voltage that it takes to drive the transducer to a level where the subject can just barely hear the test signal. These frequency-specific data are then stored and are utilized in a hearing aid fitting formula that shall be described below.

Residual hearing range is the range of hearing where an impaired ear can hear without the means of amplification. These are the frequency specific amplitudes that are above the threshold of the subject. In other words, it is the hearing that is "left over"—the sounds that are higher in amplitude than the subject's thresholds.

Amplification is a very broad expression that is used in hearing instrument terminology. A subject is said to be receiving amplification if the subject is able to hear sounds that are normally too soft to hear (the acoustic sounds are below the subject's hearing threshold). These low level sounds are amplified in order for them to be audible—sounds that cannot be heard without the amplifying device are now heard because the faint, non-audible sounds are brought to within the subject's residual dynamic range (the range that is above the threshold of the subject).

These thresholds pertaining to the invention are subject to these dynamics:
1. They are specific data that are only useful for one ear—the ear that is being tested and amplified
2. The thresholds are specific and only are pertinent to the ear level sound device
3. The thresholds are specific to the depth of the device in the ear—that is, the depth must remain constant each time the subject would insert or re-insert the in-ear device in order for the device to amplify properly
4. The threshold data cannot be transferred or referenced in any way with another subject's data
5. The data are subject to a single transducer (speaker)

Figure 2:
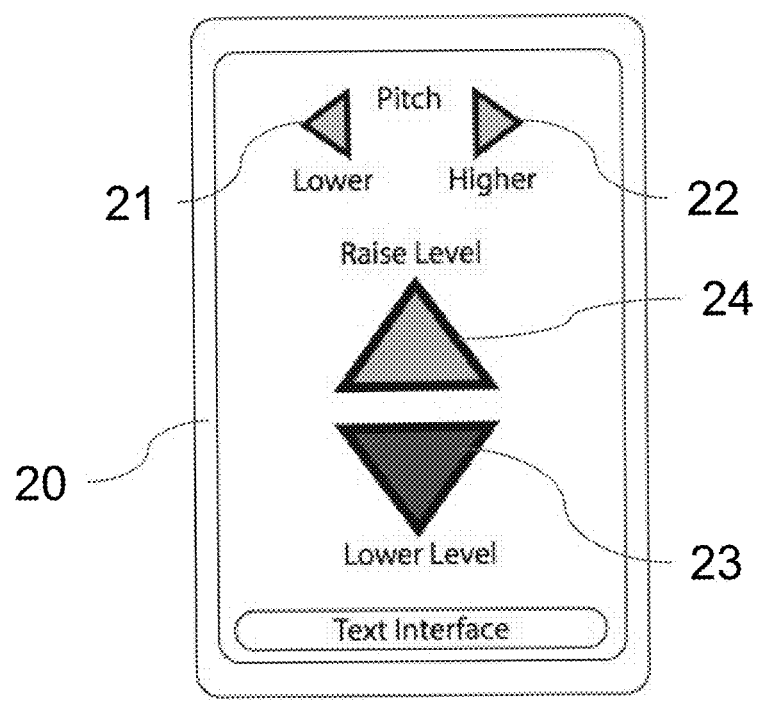
FIG. 2 shows a graphical user interface (GUI) that provides the means of visually representing and controlling auditory signals.

The threshold software presents written directions before measurement of the subject's thresholds. After this, the subject shall be presented with a simple graphical user interface (GUI) 20 that consists of four major button arrow controls 21 . . . 24, for instance the one which is depicted in FIG. 2. The amplitude arrows 23,24 are oriented in a vertical manner; these shall control the amplitude (loudness) of distinct sounds or tones at different frequencies, in this case ⅓ octave Narrow Band Noises (NBN), up and down in 2 dB steps. These noises are centred at the frequencies of 250, 500, 1000, 1500, 2000, 3000 and 4000 Hertz and are presented in a strict software based sequence consecutively from low to high. The horizontal arrow buttons 21,22 on the top of the smart phone's display allow the subject to control these centre frequencies (pitches) of the available NBN presentations or steps. Alternatively the device software may present these sounds automatically to the user at varying frequency and ascending amplitude, waiting for the user to give an appropriate response.

The apparatus that determines a subject's thresholds consists of three parts: The earpiece/amplifier in the ear, the handheld smart phone computer or other programmable device and the software on the smart phone. The earpiece/amplifier shall have an algorithm capable of receiving the target data from the smart phone and then interpreting these values into voltages that will drive the transducer at or above halfway between threshold and UCL (Uncomfortable Level) of the subject.

With the ear level device communicating with the smart phone (paired by Bluetooth or communicating over other wireless means), the subject is asked to vary the level of the first of 7 presentations of the Narrow Band noises, using the up down arrows 23,24 of the GUI of FIG. 2. The subject is instructed, by screen comments, to move the subjective loudness of this NB noise to a level where it is barely heard. Using a bracketing technique, the subject may adjust the NBN loudness to that above and below the subject threshold of hearing. When finished, the software stores the threshold SPL sound of the NBN and then the user chooses another NBN center frequency by means of the arrows on the top of the screen of the smart phone. These horizontal arrows move the center frequency band of the NBN up and down in subjective pitch.

For each NBN, the subject is asked to move through the various amplitudes of the NBNs, finding the subject's hearing threshold (again, the softest sound that the subject can hear) for every one of the NBNs. For example, the subject hears a NBN and adjusts it, with the vertical "loudness" arrows, to the sound level that is just barely heard. After this has happened, the subject hits the OK button and then the patient would receive a visual cue from the GUI (software) to move to another frequency. This may be done by clicking the horizontal (pitch) arrows 21,22 to the left or right to select another centre frequency until the NBN thresholds are recorded for all available frequencies.

After determining threshold by means of NBN and discovering the subject's dynamic range by comparing threshold data with the use of average UCL data, the software shall calculate an amplification target that is halfway between the subject's threshold and the Uncomfortable Level (UCL). Finally, the software shall present seven different speech spectra within the subject's dynamic range. The listener's task will be to pick the clearest and most pleasant spectrum. From this subjective input, the software shall decide the final amplification scheme—a sound spectrum that lays half way between the threshold and uncomfortable level—within the subject's residual dynamic range.

The large black dots indicate the amplitude/frequency coordinates that are above the SPLs of the subject's hearing thresholds. In other words, these dots represent the speaker (output transducer) voltages that produce audible SPL for the subject with the noted hearing loss. This SPL target was chosen because it is half way between threshold and UCL of the subject, and this was found to the preferred target/spectrum for many subjects.

Again, the dynamic range of hearing can be described as those sounds that have levels between the threshold of hearing, or the softest sound that one can hear, to the loudest sounds that one prefers to hear, or the uncomfortable level (UCL). Somewhere in the middle of these two ranges lays the most comfortable level (MCL). This is the target prescription of the system.

For a hearing impaired person, those sounds that lay between the threshold of hearing and the UCL is called the residual dynamic range—residual because the range is less than that of a normal hearing person and because of the elevated threshold of the hearing impaired person.

An amplification system designed to help the hearing impaired person hear better usually focuses on making speech cues more audible. Part of the design is to focus on the speech spectrum and to make as many of those sounds as possible audible to the hearing impaired person. When accomplished, the hearing impaired individual can understand speech better, mostly due to high frequency amplification of the system. (It is the high frequency range where most consonant sounds are and it is the consonants that make up most of the speech cues.)

In FIG. 8, field or area A resembles a normal hearing range, whereas the thin dashed line VI illustrates the impaired subject's threshold spectrum. The numerous small solid squares and triangles (coordinates) F+G that lay in the field above (are more intense than) the impaired threshold spectrum represent all sounds that are audible without amplification even given the impaired subject's hearing loss. A good hearing device design attempts to amplify as many sounds that are below a subject's threshold into the residual range of the impaired subject. Only then will the subject be able to hear those sounds that are below the subject's threshold.

In FIG. 8, the numerous small squares (G) and triangles (F) that lay in the field above (are more intense than) the impaired threshold spectrum VI represent those voltages that produce an SPL great enough to elicit a positive response when presented to the individual. If any of the sounds represented by the square or triangle coordinates are applied to the subject's ear, the subject will hear it without amplification.

The amplification target line, noted in FIG. 8 by the dark dotted line D connecting large dark solid circles, represents the spectrum that is halfway between the hearing threshold VI and the uncomfortable loudness level, reflected by line C, that is, it bisects the residual dynamic range F+G of the hearing impaired individual. This line D also represents the target level of the system's amplification goal; thus, it is called the system's Amplification Target Line.

The goal of the system is to amplify the faint audible sounds (triangles F) of the impaired ear and to amplify sounds that are below threshold (small dots E) into the residual dynamic range (F+G) of the subject. The system does not aim to drive the transducer by any coordinate (voltage) that is depicted in by the squares. This is the area where the hearing impaired subject can hear adequately without amplification.

SUMMARY

The ear-level hearing device of this exemplifying embodiment is controlled by a hand held computer (smart phone) with a graphical user interface designed to determine a subject's own hearing threshold, or quietest sound that an individual can hear. Hardware includes the smart phone, the viewing screen of the smart phone, smart phone software, the ear level hearing device, a transmitter on the smart phone and a receiver on the ear level device to provide communication between the graphical user interface on the smart phone to the ear level hearing device.

The interface software on the smart phone shall provide a graphical user interface (GUI), e.g. with touch screen buttons, or any other, particularly automatic, means to vary the frequency (psychoacoustic parameter is pitch) and amplitude (psychoacoustic parameter is loudness) presentation to the earpiece. Software installed on the hand-held smart phone system shall send wireless, e.g. Bluetooth, signals to the ear level device that shall change the acoustic parameters in the listening device.

The firmware/software in the ear level device shall store the frequency/amplitude parameters of the subject's thresholds and then shall wirelessly deliver them back to the smart phone for analysis. The smart phone device then shall use the threshold data to derive the appropriate amplified acoustical signal (relative to the thresholds) to the subject's ear.

The combination hearing system comprises the ear-level hearing device and the smart phone works. These work in tandem to derive a hearing impaired subject's thresholds. These thresholds are measured in terms of the voltage needed to drive the transducer to the threshold SPL. In other words, the system does not measure the actual SPL inside the canal; rather, it measures the voltage of the transducer needed to reach a subject's thresholds. From these threshold values, the system software sets a target output that is halfway between threshold and the uncomfortable level of the subject. The system then amplifies sounds that are below threshold and also faint audible sounds to within the upper part of the residual dynamic range of the listener. Various speech spectra, all lying within the residual dynamic range of the listener, are then presented in order to confirm intelligibility, comfort and pleasantness.

It will be clear that the present invention is not limited to the exemplifying embodiment thereof as presented hereinbefore. Instead a skilled person may easily devise alternative embodiments without departing from the scope or spirit of the present invention and without requiring him to exercise any inventive skill.

The invention claimed is:

1. A hearing system comprising:
a programmable sound processing means;
an ear-level hearing device having an electro-acoustic transducer that communicates with an ear canal of a subject, and a transducer driven by the programmable sound processing means on a basis of a programmable sound processing scheme;
a recording means that records a drive signal from said sound processing unit to said transducer; and
a control device to customize said sound processing scheme at least in part to said subject, wherein,
said control device comprises a temporary control device held by a user enabling the user to select auditory signals at different amplitudes,
said control device and said ear-level hearing device are provided with communication means that communicate user selected auditory signals to said transducer,
said recorder i) records the drive signal from the sound processing unit to said transducer for each of the selected auditory signal as a recording of the corresponding drive signals, and ii) provides the recording of the corresponding drive signals to said control device,
said control device comprises an algorithm that, from said recording of the corresponding drive signals, translates threshold responses of said user in response to said auditory signals into a customized sound processing scheme, and
said control device is provided with programming means that passes said customized sound processing scheme to said sound processing device.

2. The hearing system according to claim 1, wherein said drive signal comprises a drive voltage applied over said transducer.

3. The hearing system according to claim 1, wherein said auditory signals comprises narrow band noises at varying frequencies and varying amplitudes.

4. The hearing system according to claim 1, wherein said auditory signals comprise a faintest sound that the subject is capable to hear.

5. The hearing system according to claim 1, wherein said transducer is accommodated in an ear canal tip to be received in a subject's ear canal in a close fitting relationship.

6. The hearing system according to claim 5, wherein said ear canal tip comprises a exchangeable soft tip selected from a range of fitting soft tips having varying sizes.

7. The hearing system according to claim 1, wherein said control device comprises a smart phone or hand held computer loaded with software to present said auditory signals and to send said signals to said ear-level hearing device to determine the subject's thresholds.

8. The hearing system according to claim 7, wherein said software provides for a graphical user interface that provides for means of visually representing and controlling said auditory signals.

9. The hearing system according to claim 1, wherein said customized sound processing scheme resulting from said algorithm endeavours to amplify faint audible sounds and sounds that are below a hearing impaired subject's threshold into a residual dynamic range of the subject to a target that exists at least substantially halfway between a threshold level as determined of said user, particularly as measured in dB voltage, and an uncomfortable level.

10. The hearing system according to claim 1, wherein said customized sound processing scheme resulting from said algorithm endeavours to keep a hearing device output somewhere within halfway between a threshold level as determined of said user and the uncomfortable level of the subject.

11. The hearing system according to claim 1, wherein said communication means comprise wireless communication means, particularly in compliance with the Bluetooth standard.

12. A method of establishing a subject's hearing loss comprising a determination of at least one of a subject's thresholds, comprising the steps of:
using a temporarily held control device;
having the subject use, within the subject's ear, an ear-level device having a programmable sound processor driving, via a drive signal, an electro-acoustic transducer;
using a recorder connected for recording a level of the drive signal from the programmable sound processor to the transducer, recording the drive signal necessary to drive the electro-acoustic transducer in the ear of said subject to the subject's determined at least one threshold level, by obtaining a recorded signal of the drive signal in dependence on an input from the temporarily held control device to the ear-level device for making a determination of the level of the drive signal corresponding to the at least one of the subject's thresholds; and
using the recorded signal from the obtaining step as an input of the subject's threshold data to the temporarily held control device, tailoring a customized sound processing scheme transfer of the programmable sound processor driving to the subject's hearing loss.

13. The method according to claim 12 said subject's thresholds are determined for narrow band noises at varying frequencies and varying amplitudes.

14. The hearing system according to claim 2, wherein said auditory signals comprise a faintest sound that the subject is capable to hear.

15. The hearing system according to claim 3, wherein said auditory signals comprise a faintest sound that the subject is capable to hear.

16. The hearing system according to claim 1, wherein said auditory signals comprises narrow band noises at varying frequencies and varying amplitudes including one-third octave narrow band noises.

17. The hearing system according to claim 1, wherein said auditory signals comprises tone signals at varying frequencies and varying amplitudes.

18. The method according to claim 12, wherein, said recording step comprises said recorder i) recording the drive signal from the sound processing unit to the transducer for each of selected auditory signals from the control device to the ear-level device, the recording being of corresponding drive signals for each of the selected auditory signals, and ii) providing the recording of the corresponding drive signals to said control device, and said tailoring step comprises i) said control device using an algorithm that, from said recording of the corresponding drive signals, translates threshold responses of said user in response to said auditory signals into a customized sound processing scheme, ii) passing said customized sound processing scheme to said programmable processing device, and iii) programming said programmable processing device with said customized sound processing scheme.

19. A hearing system comprising an ear-level hearing device having an electro-acoustic transducer to communicate with an ear canal of a subject, which transducer is driven by programmable sound processing means on basis of a programmable sound processing scheme, and comprising a control device to customize said sound processing scheme at least in part to said subject, wherein recording means are provided to record a drive signal between said sound processing unit and said transducer, in that said control device comprises a temporary control device held by a user enabling the user to select auditory signals at different amplitudes, in that said control device and said ear-level hearing device are provided with communication means to communicate user selected auditory signals to said transducer and to exchange corresponding drive signals as recorded by said recording means with said control device, in that said control device comprises an algorithm to translate threshold responses of said user in response to said auditory signals into a customized sound processing scheme, and in that said control device is provided with programming means to pass said customized sound processing scheme to said sound processing device wherein said customized sound processing scheme resulting from said algorithm endeavours to keep a hearing device output somewhere within halfway between a threshold level as determined of said user and the uncomfortable level of the subject.

* * * * *